(12) United States Patent
Medintz et al.

(10) Patent No.: US 9,120,967 B2
(45) Date of Patent: Sep. 1, 2015

(54) CONCENTRIC FORSTER RESONANCE ENERGY TRANSFER RELAY FOR THE PARALLEL DETECTION OF TWO BIO/PHYSICOCHEMICAL PROCESS

(71) Applicants: Igor L. Medintz, Springfield, VA (US); W. Russ Algar, Vancouver (CA)

(72) Inventors: Igor L. Medintz, Springfield, VA (US); W. Russ Algar, Vancouver (CA)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 69 days.

(21) Appl. No.: 14/201,279

(22) Filed: Mar. 7, 2014

(65) Prior Publication Data

US 2014/0264262 A1    Sep. 18, 2014

Related U.S. Application Data

(60) Provisional application No. 61/782,098, filed on Mar. 14, 2013.

(51) Int. Cl.
| | | |
|---|---|---|
| H01L 29/06 | (2006.01) |
| H01L 21/00 | (2006.01) |
| H01L 33/26 | (2010.01) |
| C09K 11/02 | (2006.01) |
| C09K 11/06 | (2006.01) |
| C09K 11/56 | (2006.01) |
| C09K 11/88 | (2006.01) |
| G01N 21/64 | (2006.01) |
| G01N 33/58 | (2006.01) |
| G01N 33/542 | (2006.01) |
| A61K 49/00 | (2006.01) |
| H01L 33/06 | (2010.01) |
| H01L 51/56 | (2006.01) |

(52) U.S. Cl.
CPC ............. *C09K 11/02* (2013.01); *A61K 49/0093* (2013.01); *C09K 11/025* (2013.01); *C09K 11/06* (2013.01); *C09K 11/565* (2013.01); *C09K 11/883* (2013.01); *G01N 21/6428* (2013.01); *G01N 33/542* (2013.01); *G01N 33/582* (2013.01); *G01N 33/588* (2013.01); *G01N 2021/6441* (2013.01); *H01L 21/00* (2013.01); *H01L 33/06* (2013.01); *H01L 51/56* (2013.01)

(58) Field of Classification Search
CPC ......... H01L 33/32; H01L 33/06; H01L 51/56; H01L 27/32; H01L 29/155; H01L 27/3244; H01L 27/3211; C09K 11/06; B82Y 20/00
USPC ......... 257/13, 17, E33.005, E33.061, E33.08, 257/E21.459; 438/22, 28, 29, 47; 977/840, 977/774
See application file for complete search history.

(56) References Cited

U.S. PATENT DOCUMENTS

2010/0075361 A1* 3/2010 Mattoussi et al. .............. 435/29
2010/0264333 A1* 10/2010 Offermans et al. ........ 250/459.1

* cited by examiner

*Primary Examiner* — Thinh T Nguyen
(74) *Attorney, Agent, or Firm* — US Naval Research Laboratory; Roy Roberts

(57) ABSTRACT

Described herein is a Förster (or fluorescence) resonance energy transfer (FRET) configuration with three energy transfer pathways between three luminescent components, where two of the energy transfer steps occur in sequence as a relay, and the first step of the relay is in competition with a third energy transfer process (energy transfer from the donor to the intermediary is in competition with energy transfer from the donor directly to the terminal acceptor).

14 Claims, 7 Drawing Sheets

US 9,120,967 B2

CONCENTRIC FORSTER RESONANCE ENERGY TRANSFER RELAY FOR THE PARALLEL DETECTION OF TWO BIO/PHYSICOCHEMICAL PROCESS

CROSS-REFERENCE TO RELATED APPLICATIONS

This application claims the benefit of U.S. Provisional Application 61/782,098 filed on Mar. 14, 2013, the entirety of which is incorporated herein by reference.

BACKGROUND

Conventional Förster (or fluorescence) resonance energy transfer (FRET) configurations typically comprise two fluorescent dyes assembled into discrete pairs. Energy transfer is observed in a single step from the donor to the acceptor. This basic format is sufficient for many applications and is, by far, the most commonly reported in the scientific literature. Several commercial products (e.g., molecular beacons, TaqMan probes) also rely on discrete FRET pairs. More complex FRET configurations with multiple energy transfer steps have also been described, where energy is transferred from an initial donor to a terminal acceptor in n successive steps through n−1 intermediary dyes that act as both an acceptor (for the previous dye in the sequence) and donor (for the next dye in the sequence). The common feature of these configurations is that the FRET relays are designed to extend the range of energy transfer to distances greater than that allowed by the constraints of one-step FRET (i.e., >1.5-times the Förster distance, or typically >6 nm). As such, the configurations are typically linear, pseudo-linear, or otherwise comprise a sequential geometric arrangement where the excitation energy moves further out into space from its origin at the initial donor.

BRIEF SUMMARY

In a first embodiment, a FRET relay assembly includes a semiconductor quantum dot (QD) configured as FRET donor; a first fluorescent dye configured as FRET acceptor to the QD in a first FRET process; and a second fluorescent dye configured as a FRET acceptor in both (a) a second FRET process wherein the first fluorescent dye is a donor, and (b) a relatively inefficient third FRET process wherein the QD is a donor, wherein the first and second fluorescent dyes are assembled to the QD at approximately the same distance as each other, and in sufficient proximity thereto so as to allow for the three FRET processes to occur.

In another embodiment, a method of preparing a FRET relay assembly includes binding semiconductor quantum dots (QDs) to a first fluorescent dye and a second fluorescent dye to obtain a FRET relay assembly according to the first embodiment.

In a further embodiment, a method of using FRET relay assemblies includes providing a population of FRET relay assemblies according to the first embodiment, wherein the first and second fluorescent dyes are assembled to the QD via first and second separable linkages, respectively, and subjecting the first and/or second separable linkages to separation.

Ensemble PL spectra for $[Sub_{ChT}(A555)]_M$-QD-$[Sub_{TRP}(A647)]_N$ conjugates are depicted at values of N=0-7 and M=0-7 in FIGS. 3A through 3H. Each sub-figure corresponds to a unique value of M, the number of A555 per QD. The arrows indicate the trends in PL as N, the number of A647 per QD, increased. The QD, A555, and A647 PL contributions are labeled in FIG. 3H. Note that the scale of the y-axis changes from (A)-(H). The excitation wavelength was 400 nm.

Figure 4:
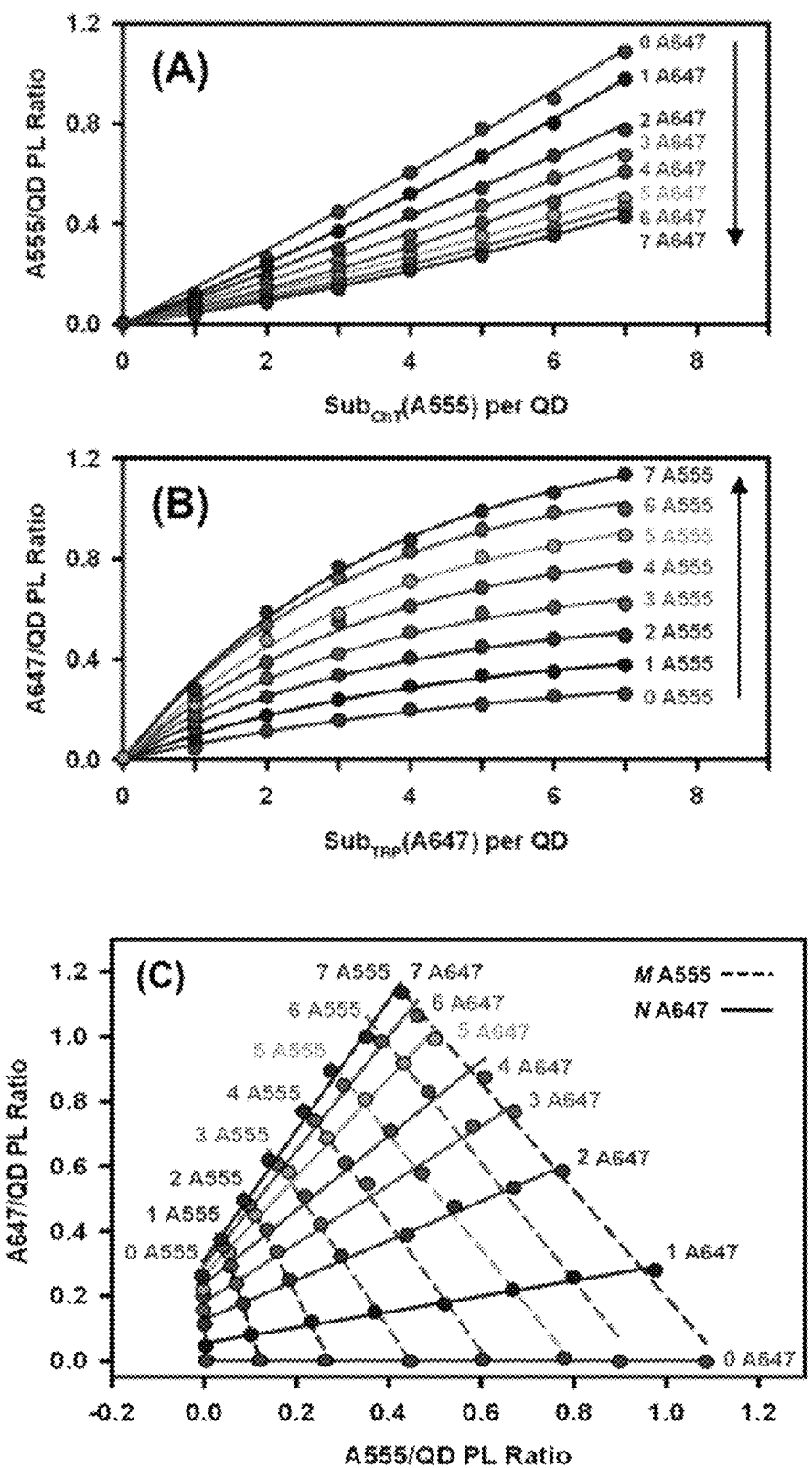

FIGS. 4A and 4B show changes in the A555/QD PL ratio and the A647/QD PL ratio, respectively, as a function of the average number of $Sub_{ChT}(A555)$, M, and $Sub_{TRP}(A647)$, N, per QD. (C) A647/QD PL ratios plotted versus A555/QD PL ratios. Each combination of PL ratios (i.e. point on the plot) corresponds to a unique combination (M, N).

FIG. 5A illustrates a schematic of a TRP sensing experiment with $FRET_1$, $FRET_2$ and $FRET_3$ indicated by 1, 2 and 3, respectively. FIG. 5B shows (i) A555/QD and (ii) A647/QD PL ratios and (C) corresponding activity data for the digestion of (i) SubChT and (ii) SubTRP in $[Sub_{ChT}(A555)]_5$-QD-$[Sub_{TRP}(A647)]_5$ conjugates by different concentrations of TRP. The combined PL data (B,i-ii) is utilized to calculate the progress curves shown in FIG. 5C, i and ii. Note the lack of any non-specific ChT activity in this experiment.

FIG. 6A illustrates a schematic of the TRP+ChT sensing experiment with $FRET_1$, $FRET_2$ and $FRET_3$ indicated by 1, 2 and 3, respectively. FIG. 6B shows (i) A555/QD and (ii) A647/QD PL ratios and FIG. 6C shows corresponding activity data for the digestion of (i) SubChT and (ii) SubTRP in $[Sub_{ChT}(A555)]_5$-QD-$[Sub_{TRP}(A647)]_5$ conjugates by different concentrations of TRP+40 nM ChT. The combined PL data (B,i-ii) is utilized to calculate the progress curves (FIG. 6C, i-ii). The activity in the top panel in FIG. 6C is constant as a fixed amount of ChT was used versus the different concentrations of TRP (bottom).

FIG. 7A illustrates a schematic of the pro-ChT activation sensing experiment with FRET1, FRET2 and FRET3 indicated by 1, 2 and 3, respectively. (B) (i) A555/QD and (ii) A647/QD PL ratios and (C) corresponding activity data for the digestion of (i) SubChT and (ii) SubTRP in $[Sub_{ChT}(A555)]_5$-QD-$[Sub_{TRP}(A647)]_5$ conjugates by different concentrations of TRP+39 nM pro-ChT. The combined PL data (FIG. 7B,i-ii) is utilized to calculate the progress curves seen in FIG. 7C. The arrow in FIG. 7C,i indicates the approximate inflection point.

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used in this specification and the appended claims, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

DESCRIPTION

Described herein is a Förster (or fluorescence) resonance energy transfer (FRET) configuration with three energy transfer pathways between three luminescent components, where two of the energy transfer steps occur in sequence as a relay, and the first step of the relay is in competition with a third energy transfer process (energy transfer from the donor to the intermediary is in competition with energy transfer from the donor directly to the terminal acceptor). The terminology, "concentric" refers to the fact that, (i) in contrast to typical FRET relays, this FRET relay does not move the excitation energy further away from the initial donor than the first energy transfer step, and (ii) that multiple copies of two of the luminescent component are assembled approximately centrosymmetrically around the first component. Potential applications include sale and use in areas where luminescent probes or reporters in biological applications may require, or benefit from, multiplexed detection in a spectral format with only one type of probe. This includes imaging, assays, and chemo/biosensing in vitro or within cells and tissues.

In a reduction to practice, a luminescent CdSe/ZnS quantum dot (QD) was used as the initial FRET donor with Alexa Fluor 555 (A555) and Alexa Fluor 647 (A647) fluorescent dyes as subsequent FRET acceptors. The FRET pathways include energy transfer from the QD to the A555, from the A555 to the A647 (the relay), and from the QD to the A647. Unique combinations of photoluminescence are obtained from different combinations of A555 and A647 assembled per QD, permitting use of the concentric FRET relay for the parallel detection of two bio/physicochemical processes using one probe entity, which is in contrast to the current state-of-the-art of using this separate probe entities to detect each bio/physicochemical process of interest. This concentric FRET relay operated to quantitatively measure the activity of two proteolytic enzymes in parallel.

Figure 1A:
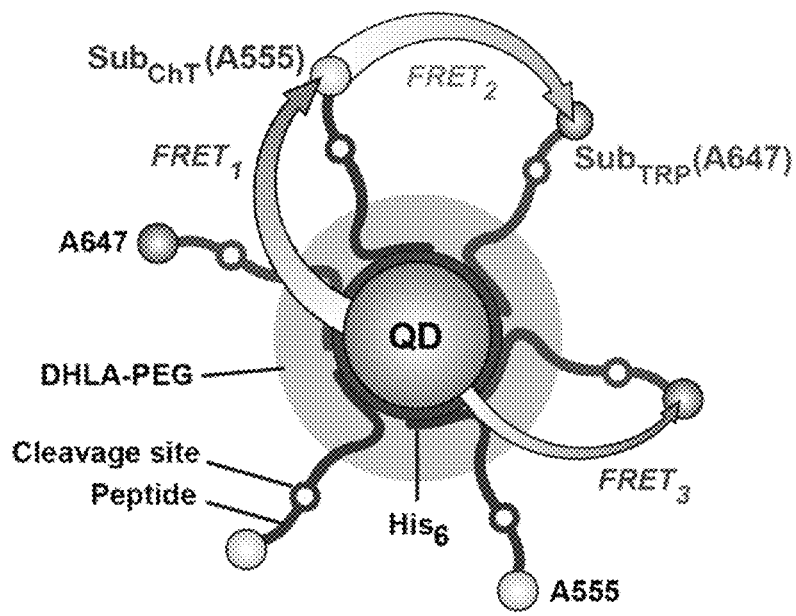
FIG. 1A illustrates the design of an exemplary FRET relay assembly and three possible energy transfer pathways between the QD, A555, and A647. The dye-labeled peptide substrates (Sub) are assembled to poly(ethylene glycol) ligand (DHLA-PEG)-coated CdSe/ZnS QDs via polyhistidine ($His_6$) tails.
Figure 1B:
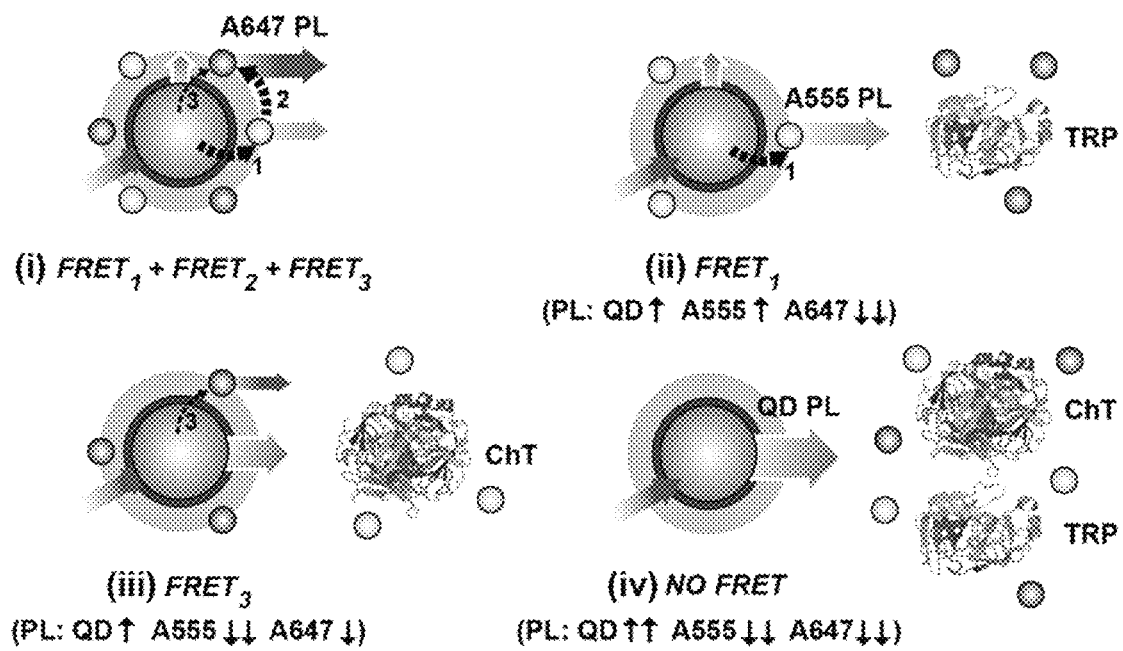
FIG. 1B shows qualitative changes in PL from the three emitters as a function of trypsin (TRP) and chymotrypsin (ChT) activity. The sizes of the colored arrows reflect the magnitude of the PL intensities.
Figure 2:
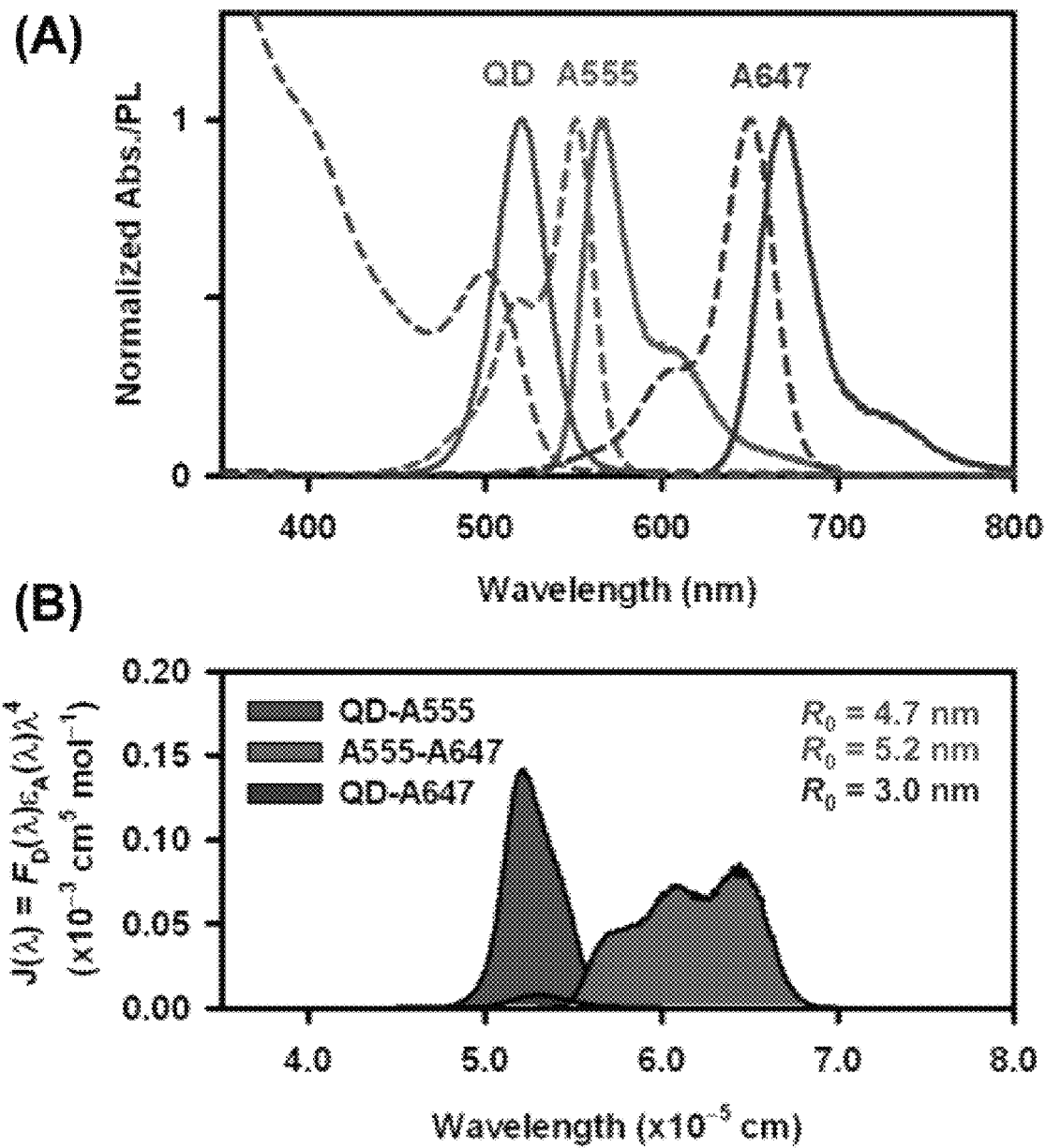
FIG. 2A illustrates absorption (dashed lines) and emission (solid lines) spectra for the QD, A555, and A647.
FIG. 2B shows spectral overlap functions for the QD-A555, A555-A647, and QD-A647 FRET pairs. The Förster distances are also listed for each pair.
Figure 3:
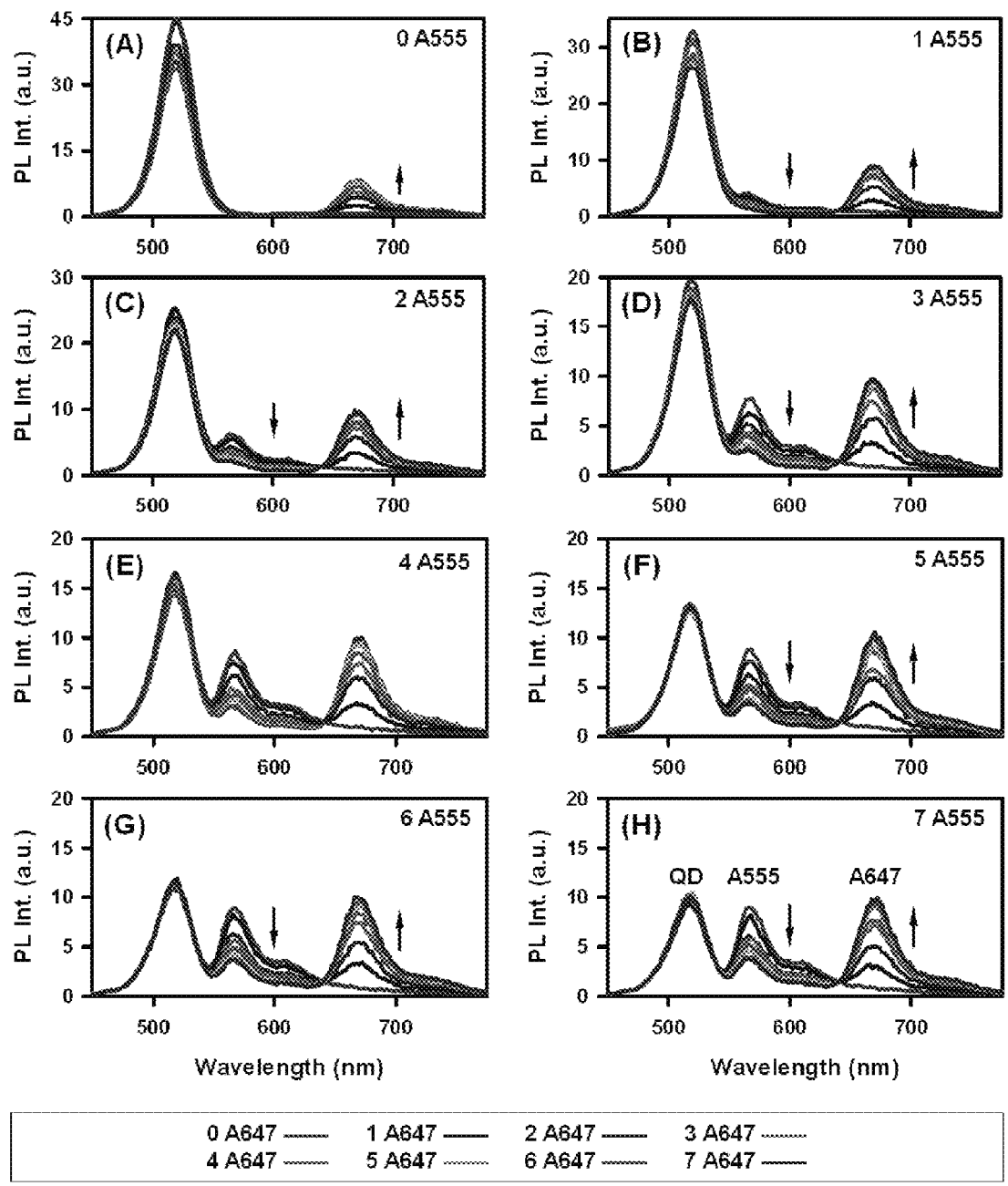

As noted herein, a FRET configuration is designed with a two-step relay in which the excitation energy is not moved any further from the donor, and energy transfer from the donor to the intermediary is in competition with energy transfer from the donor directly to the terminal acceptor. Further, the FRET configuration does not comprise discrete donor-acceptor FRET pairs, but rather three coupled one donor-multiple acceptor configurations. In an embodiment illustrated in FIGS. 1A and 1B, Alexa Fluor 555 (A555) and Alexa Fluor 647 (A647) fluorescent dyes are co-assembled around a central CdSe/ZnS quantum dot (QD) scaffold. The QD serves as the initial donor and the most efficient energy transfer pathway is a relay from the QD to the A555 (FRET1) and then from the A555 to the A647 (FRET2). However, because the A647 is co-assembled at a approximately the same distance from the QD as the A555 (instead of a linear/sequential construct), direct energy transfer for the QD to the A647 (FRET3) is also a viable option, even though this energy transfer pathway is much less efficient. The spectral overlap and Forster distance for each FRET pair are shown in FIG. 2B, and determine the rate/efficiency of each FRET process. Note that although there are multiple A555 and A647 dyes assembled to each QD, FRET2 remains a one donor-multiple acceptor configuration because (i) the system can be optically excited at 400 nm to avoid direct excitation of the A555 and A647, and (ii) the QD can only transfer its excitation energy to any one of the assembled A555 dye molecules, but only one per excitation event. The competition between the FRET1 and FRET3 pathways can be tuned based on the average number of co-assembled A555 (M) and A647 (N) per QD. Importantly, different (M, N) combinations can be resolved through fluorescence measurements because each yields a unique combination of A555/QD and A647/QD PL ratios. Measurement of the QD, A555, and A647 PL thus permits determination of (M, N) through prior calibration of the PL ratios. An example of a calibration is shown FIGS. 3-4. Parameterized mathematical calibration functions (or other chemometric methods) can be used to calculate values of M and N from the PL measurements.

A FRET configuration that permits determination of M and N could potentially be designed without a FRET2 relay, provided that FRET1 and FRET3 have comparable efficiencies. However, to obtain comparable FRET1 and FRET3 efficiencies, the corresponding acceptors would need to have comparable spectral overlap with the QD donor. Almost invariably, dyes with similar absorption spectra (the key determinant of spectral overlap) have similar emission spectra, and thus the sensitization of the FRET1 acceptor vs. FRET3 acceptor would be exceedingly difficult to resolve in PL measurements. The use of a very efficient FRET2 pathway herein allows for use of two fluorescent dyes (A555 and A647) with largely resolved emission spectra that are easily measured. It is the unique combination of the different efficiencies for FRET1 and FRET3, and the efficient FRET2 relay, that make our invention particularly suitable for detecting two bio/physicochemical process in parallel. The CdSe/ZnS QD, A555, and A647 were selected for reduction to practice but are not limiting. The QD is critical because it provides an effective scaffold for assembly of the A555 and A647 at similar distances and controllable valences (i.e. ratios of peptide assembled/QD) using peptide bridges; however, embodiments could be readily constructed using other QD materials or colors of QD PL, or even a different luminescent nanoparticle scaffold of similar size and comparable emission properties. Many other fluorescent dyes could be used in addition to A555 and A647, as could many alternative molecular bridges between the central initial donor and peripheral acceptors, provided that the dimensionality remained commensurate with the Förster distances and the relative rates for the three FRET process were comparable.

Figure 5:
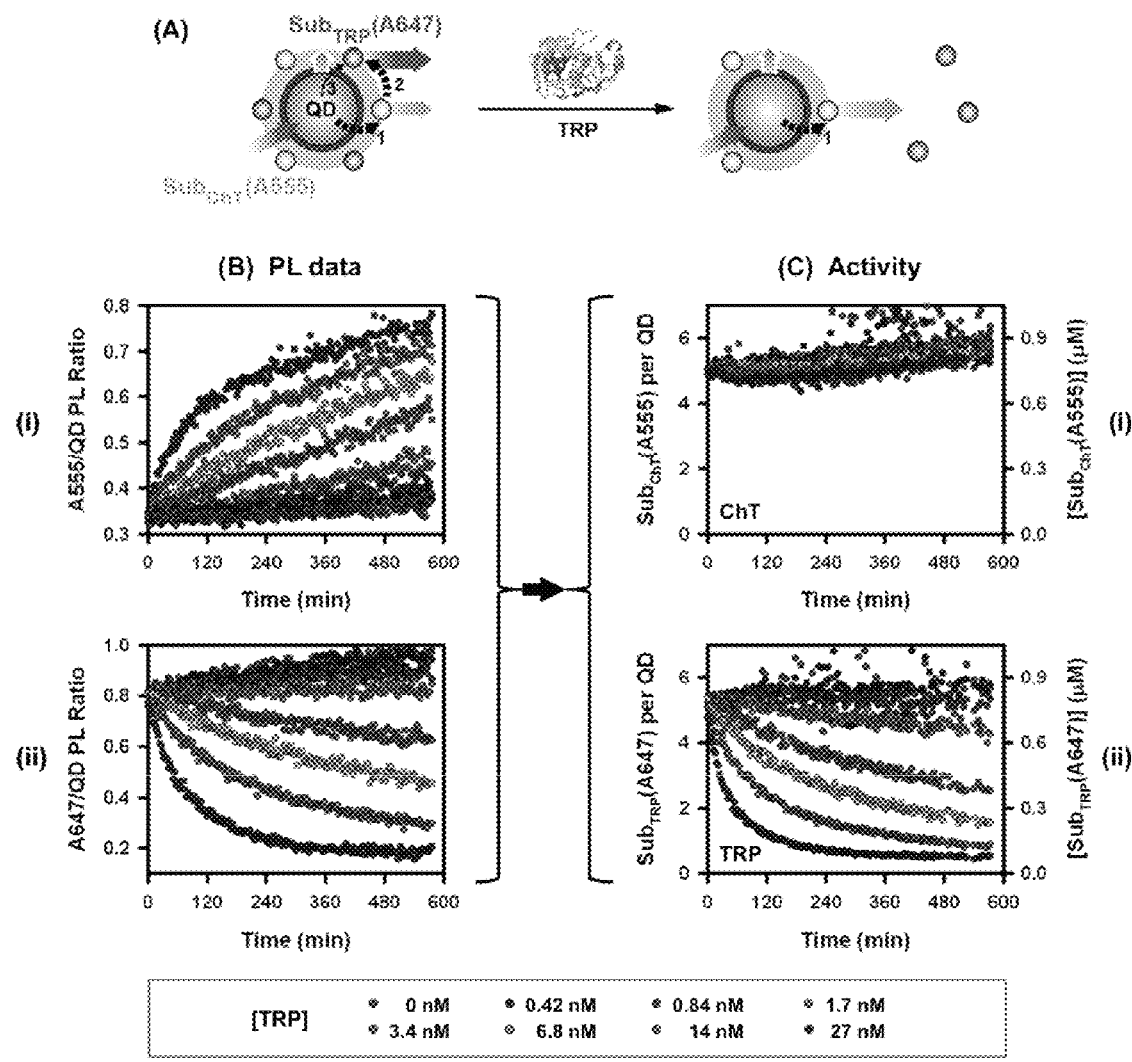
Figure 6:
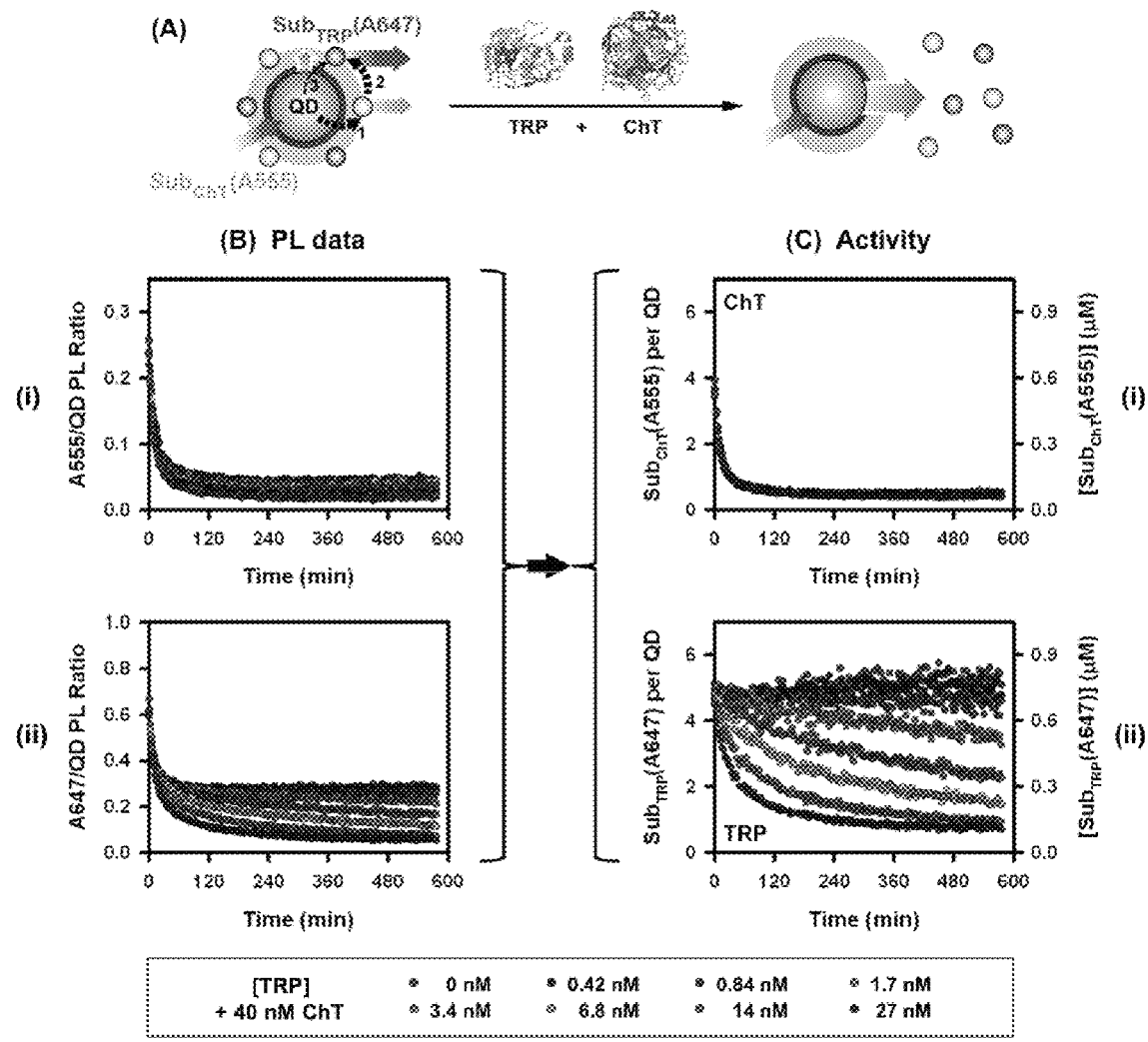
Figure 7:
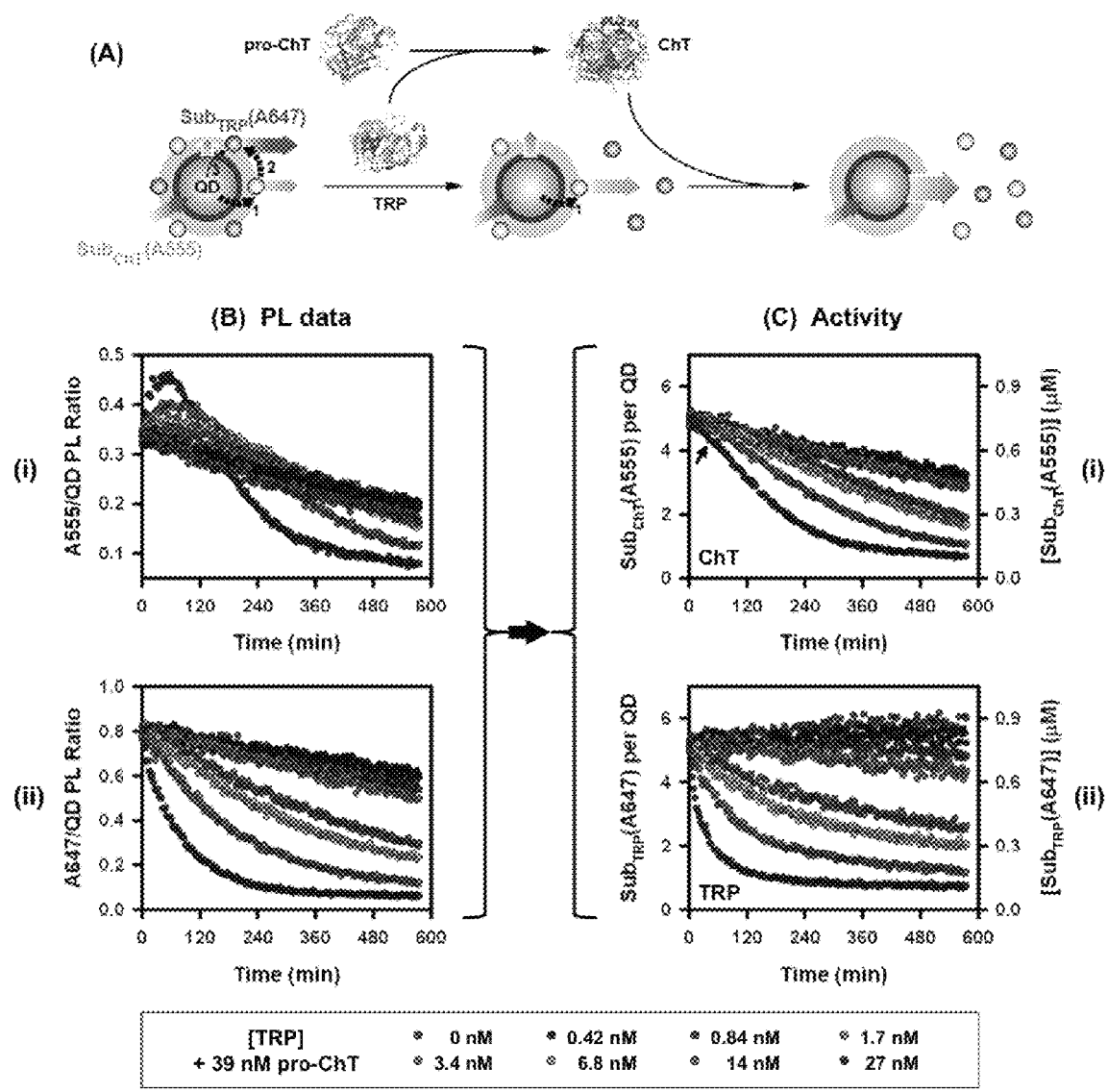

To demonstrate the ability of this technique to detect two bio/physicochemical process, tests were made using the peptide bridge between the QD and A555 (termed $Sub_{ChT}$(A555) and having SEQ ID No: 1) as substrate for chymotrypsin, a proteolytic enzyme, and choose the peptide bridge between the QD and A647 (termed $Sub_{TRP}$(A647) and having SEQ ID No: 2) to be a substrate for trypsin, another proteolytic enzyme with different specificity. Testing occurred in three stages. Changes in QD, A555, and A647 PL were monitored upon (i) exposure to different concentrations of trypsin; (ii) different concentrations of trypsin in the presence of a fixed concentration of chymotrypsin; and (iii) different concentrations of trypsin in the presence of a fixed concentration of chymotrypsinogen. Chymotrypsinogen is a low-activity precursor of chymotrypsin, which is activated to chymotrypsin by trypsin. Calculation of the A555/QD and A647/QD PL ratios from the measured PL data permitted determination of the activity of the trypsin and chymotrypsin. The results for these three tests are shown in FIGS. 5-7, and clearly show the ability to detect trypsin and chymotrypsin independently along with the ability to monitor the activity of one protein (trypsin) as it activates another (chmytrypsinogen). Table 1 lists trypsin kinetic constants derived from the data, further confirming the independent detection of trypsin and chymotrypsin. Other biological or non-biological process could be measured using such a technique, provided that suitable bridging biomolecules, receptors, or other molecular components were used to assemble the concentric FRET relay.

TABLE 1

Comparison of the specificity constants ($k_{cat}/K_m$) for each concentration of TRP used in the three protease assays as determined using the concentric FRET relay invention.

| | $k_{cat}/K_m$ ($s^{-1}$ $mM^{-1}$) | | | | |
|---|---|---|---|---|---|
| [TRP] (nM) | 3.4 | 6.8 | 14 | 27 | Ave.[a] |
| TRP | 8.1 | 14.3 | 12.4 | 14.2 | 12 ± 3 |
| TRP + ChT[b] | 24.3 | 20.4 | 19.1 | 13.9 | 19 ± 4 |
| TRP + pro-ChT[c] | 7.9 | 10.8 | 14.1 | 17.9 | 13 ± 4 |

[a]One standard deviation is reported.
[b]40 nM ChT.
[c]39 nM pro-ChT.

Advantages and Applications

The concentric FRET relay provides two analytic optical signals (PL ratios) as a single entity (cf. two or more one-step FRET pairs). The concentric FRET relay provides two analytic optical signals with excitation at only one wavelength (or one narrow band of wavelengths). The concentric FRET relay avoids the challenges associated with the use of two different probes; for example, discrepancies in the magnitude of the optical signals from two different probes, discrepancies in biological activity between two different probes, discrepancies in the delivery or distribution of two different probes. FRET1, FRET2, and FRET3 can be tuned by controlling the number of initial donors and terminal acceptors, respectively, associated with the QD. Three-fold flexibility in tuning of FRET1, FRET2, and FRET3 by selection of the central QD and two fluorescent dyes to increase or decrease spectral overlap integrals. FRET1, FRET2, and FRET3 can be tuned by varying the distance (i.e., length of the molecular bridge) between the central QD and the two fluorescent dyes. The two-step FRET relay can potentially be used in solution, at an interface, or within cellular or tissue environments. Detection is preferably based entirely on basic PL intensity measurements. The concentric FRET relay can be calibrated and used as a probe with filter- or monochromator-based fluorescence instruments. The QD FRET relay assembly is directly amenable to multiphoton excitation which would provide nearly "pure" FRET signal (almost no background from direct acceptor excitation) while greatly facilitating in vivo applications.

Other Techniques

An alternative that provides two analytic optical signals for one population of QDs is the use of a QD-fluorescent dye FRET pair in combination with a second fluorescent dye. This second fluorescent dye does not participate in FRET, but is nonetheless assembled to the QD and can be directly optically excited at the same time as the QD (see C. Y. Zhang and J. Hu, "Single Quantum Dot-Based Nanosensor for Multiple DNA Detection." Anal. Chem. 2010. 82(5): 1921-1927). This methodology is only applicable with single particle fluorescence measurements and microfluidic flow of a sample. In contrast, the technique described here is compatible with both ensemble and (in principle) single particle measurements, and a variety of analytical formats including, but not limited to, bulk solution, microfluidic chips, extra/intracellular environments, tissue, or in vivo. The concentric FRET relay does not have specific flow requirements, and requires far less sophisticated instrumentation for implementation and analysis.

Two related patent documents (each incorporated herein by reference) can be considered in view of this invention. US Patent Publication No. 2012-0248409 ("the '409 publication") describes the concurrent use of charge transfer quenching and FRET to generate two analytical signals from a QD. The advantage of the technique described herein over that of the '409 publication is that measurements here are entirely ratiometric, whereas the technique in the '409 publication relies on absolute intensity measurements which are less reliable in many applications. U.S. Pat. No. 8,476,083 describes generation of two analytical signals from a QD using a spectro-temporal FRET relay; however, this method relies on time-gated fluorescence measurements which are not a routine capability of most fluorescence instrumentation, especially fluorescence microscopes. It also generally uses a luminescent lanthanide complex to initiate the spectro-temporal FRET relay, and the selection of these complexes that are available is quite limited. In contrast, the technique described here does not require time-gating and can be used (or adapted) for almost all standard fluorescence instrumentation, including fluorescence microscopes, while being compatible with a wide array of commercially available fluorescent dyes.

CONCLUDING REMARKS

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

Basic Principles and Applications of FRET

J. R. Lakowicz, *Principles of Fluorescence Spectroscopy*, 3rd Ed.; Springer; New York, 2006.
P. G. Wu, L. Brand, "Resonance Energy Transfer—Methods and Applications" *Anal. Biochem.* 1994, 218, 1-13 (review).
E. A. Jares-Erijman, T. M. Jovin, "FRET Imaging" *Nat. Biotechnol.* 2003, 21, 1387-1395.
P. R. Selvin, "The renaissance of fluorescence resonance energy transfer" *Nat. Struct. Biol.* 2000, 7, 730-734.
P. R. Selvin, "Fluorescence resonance energy transfer" *Meth. Enzymol.* 1995, 246, 300-334.
R. M. Clegg, "Fluorescence resonance energy transfer and nucleic-acids" Meth. Enzymol. 1992, 211, 353-388.

G. D. Scholes, "Long-range resonance energy transfer in molecular systems" *Ann. Rev. Phys. Chem.* 2003, 54, 57-87.

S. Weiss, "Measuring conformational dynamics of biomolecules by single molecule fluorescence spectroscopy" *Nat. Struct. Biol.* 2000, 7, 724-729.

Quantum Dots in FRET Pairs

W. R. Algar, K. Susumu, J. B. Delehanty, I. L. Medintz, "Quantum Dots in Bioanalysis: Crossing the Valley of Death" *Anal. Chem.* 2011, 83, 8826-8837 (review).

W. R. Algar, U. J. Krull, "New opportunities in multiplexed optical bioanalyses using quantum dots and donor-acceptor interactions" *Anal. Bioanal. Chem.*, 2010, 398, 2439-2449 (review).

W. R. Algar, A. J. Tavares, U. J. Krull, "Beyond labels: A review of the application of quantum dots as integrated components of assays, bioprobes, and biosensors utilizing optical transduction" *Anal. Chim. Acta*, 2010, 673, 1-25 (review).

I. L. Medintz, H. Mattoussi, "Quantum dot-based resonance energy transfer and its growing application in biology" *Phys. Chem. Chem. Phys.*, 2009, 11, 17-45 (review).

K. E. Sapsford, L. Berti, I. L. Medintz, "Materials for fluorescence resonance energy transfer analysis: Beyond traditional donor-acceptor combinations" *Angew. Chem. Int. Ed.*, 2006, 45, 4562-4588 (review).

What is claimed is:

1. A FRET relay assembly comprising:
   a semiconductor quantum dot (QD) configured as FRET donor;
   a first fluorescent dye configured as FRET acceptor to the QD in a first FRET process; and
   the second fluorescent dye configured as a FRET acceptor in both (a) a second FRET process wherein the first fluorescent dye is a donor, and (b) a relatively inefficient third FRET process wherein the QD is a donor,
   wherein the first and second fluorescent dyes are assembled to the QD at approximately the same distance as each other, and in sufficient proximity thereto so as to allow for the three FRET processes to occur.

2. The FRET relay assembly of claim 1, wherein said first and/or second fluorescent dyes are assembled to the QD via a separable linkage.

3. The FRET relay assembly of claim 2, wherein said separable linkage is separable by a protease.

4. The FRET relay assembly of claim 2, wherein each said first and second fluorescent dyes are assembled to the QD via a different separable linkage.

5. The FRET relay assembly of claim 4, wherein said different separable linkages are separable by different proteases.

6. A method of preparing a FRET relay assembly, the method comprising:
   binding semiconductor quantum dots (QDs) to a first fluorescent dye and to a second fluorescent dye to obtain a FRET relay assembly wherein
   the QD is configured as FRET donor;
   the first fluorescent dye configured as FRET acceptor to the QD in a first FRET process; and
   the second fluorescent dye configured as a FRET acceptor in both (a) a second FRET process wherein the first fluorescent dye is a donor, and (b) a relatively inefficient third FRET process wherein the QD is a donor,
   wherein the first and second fluorescent dyes are assembled to the QD at approximately the same distance as each other, and in sufficient proximity thereto so as to allow for the three FRET processes to occur.

7. The method of claim 6, wherein said first and/or second fluorescent dyes are assembled to the QD via a separable linkage.

8. The method of claim 7, wherein said separable linkage is separable by a protease.

9. The method of claim 7, wherein each said first and second fluorescent dyes are assembled to the QD via a different separable linkage.

10. The method of claim 7, wherein said different separable linkages are separable by different proteases.

11. A method of using FRET relay assemblies, the method comprising:
    providing a population of FRET relay assemblies, each such FRET relay assembly comprising:
        a semiconductor quantum dot (QD) configured as FRET donor;
        a first fluorescent dye configured as FRET acceptor to the QD in a first FRET process; and
        a second fluorescent dye configured as a FRET acceptor in both (a) a second FRET process wherein the first fluorescent dye is a donor, and (b) a relatively inefficient third FRET process wherein the QD is a donor,
        wherein the first and second fluorescent dyes are assembled to the QD via first and second separable linkages, respectively, at approximately the same distance as each other, and in sufficient proximity thereto so as to allow for the three FRET processes to occur; and
    subjecting the first and/or second separable linkages to separation.

12. The method of claim 11, further comprising first preparing said FRET relay assemblies by binding the QDs to the first fluorescent dye and to the second fluorescent dye.

13. The method of claim 11, wherein said separation comprises proteolysis.

14. The method of claim 13, wherein said first separable linkage and said second separable linkage are cleaved by different proteases.

* * * * *

SEQUENCE LISTING

```
<160> NUMBER OF SEQ ID NOS: 2

<210> SEQ ID NO 1
<211> LENGTH: 29
<212> TYPE: PRT
<213> ORGANISM: Artificial Sequence
<220> FEATURE:
<223> OTHER INFORMATION: synthetic construct

<400> SEQUENCE: 1

Cys Ser Ala Tyr Ala Ala Thr Asp Glu Gly Asn Gln Gly Thr Ser Pro
1               5                   10                  15

Pro Pro Pro Pro Pro Pro Ser His His His His His His
            20                  25

<210> SEQ ID NO 2
<211> LENGTH: 29
<212> TYPE: PRT
<213> ORGANISM: Artificial Sequence
<220> FEATURE:
<223> OTHER INFORMATION: synthetic construct

<400> SEQUENCE: 2

Cys Ser Thr Arg Thr Asp Glu Gly Asn Gln Gly Gly Thr Ser Ser Pro
1               5                   10                  15

Pro Pro Pro Pro Pro Pro Ser His His His His His His
            20                  25
```